(12) United States Patent
Patel et al.

(10) Patent No.: US 9,546,121 B2
(45) Date of Patent: Jan. 17, 2017

(54) PROCESS FOR MAKING PHENOL AND/OR CYCLOHEXANONE

(71) Applicant: ExxonMobil Chemical Patents Inc., Baytown, TX (US)

(72) Inventors: Bryan A. Patel, Jersey City, NJ (US); Jihad M. Dakka, Whitehouse Station, NJ (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/031,759

(22) PCT Filed: Oct. 17, 2014

(86) PCT No.: PCT/US2014/061088
§ 371 (c)(1),
(2) Date: Apr. 25, 2016

(87) PCT Pub. No.: WO2015/076954
PCT Pub. Date: May 28, 2015

(65) Prior Publication Data
US 2016/0264501 A1 Sep. 15, 2016

Related U.S. Application Data

(60) Provisional application No. 61/907,844, filed on Nov. 22, 2013.

(30) Foreign Application Priority Data

Feb. 4, 2014 (EP) .................................... 14153808

(51) Int. Cl.
| | |
|---|---|
| C07C 45/53 | (2006.01) |
| C07C 37/08 | (2006.01) |
| C07C 407/00 | (2006.01) |
| C07C 37/72 | (2006.01) |
| C07C 7/10 | (2006.01) |
| B01J 31/02 | (2006.01) |

(52) U.S. Cl.
CPC ............ *C07C 37/08* (2013.01); *B01J 31/0247* (2013.01); *C07C 7/10* (2013.01); *C07C 37/72* (2013.01); *C07C 45/53* (2013.01); *C07C 407/00* (2013.01); *C07C 407/003* (2013.01); *C07C 2101/14* (2013.01); *C07C 2101/16* (2013.01)

(58) Field of Classification Search
CPC ....... C07C 45/53; C07C 37/08; C07C 407/003
USPC ................................ 568/342, 347, 798, 570
See application file for complete search history.

(56) References Cited

U.S. PATENT DOCUMENTS

| | | |
|---|---|---|
| 4,169,857 A | 10/1979 | Murtha |
| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,362,697 A | 11/1994 | Fung et al. |
| 6,037,513 A | 3/2000 | Chang et al. |
| 6,077,498 A | 6/2000 | Diaz Cabanas et al. |
| 6,730,625 B1 | 5/2004 | Chang et al. |
| 6,756,030 B1 | 6/2004 | Jan et al. |
| 7,579,511 B1 | 8/2009 | Dakka et al. |

FOREIGN PATENT DOCUMENTS

| | | |
|---|---|---|
| EP | 0 293 032 | 11/1988 |
| WO | 97/17290 | 5/1997 |
| WO | 2009/128984 | 10/2009 |
| WO | 2009/131769 | 10/2009 |
| WO | 2011/031374 | 3/2011 |
| WO | 2011/100013 | 8/2011 |
| WO | 2012/036820 | 3/2012 |
| WO | 2012/036822 | 3/2012 |
| WO | 2012/134549 | 10/2012 |
| WO | 2014/209557 | 12/2014 |
| WO | 2014/209578 | 12/2014 |

*Primary Examiner* — Sikarl Witherspoon
(74) *Attorney, Agent, or Firm* — Siwen Chen; Stephen A. Baehl (57) ABSTRACT

A process for making phenol and/or cyclohexanone comprises: (A) oxidizing a cyclohexylbenzene feed to obtain an oxidation product comprising cyclohexylbenzene, cyclohexyl-1-phenyl-1-hydroperoxide and phenol; (B) separating at least a portion of the oxidation product to obtain a first fraction comprising cyclohexyl-1-phenyl-1-hydroperoxide and a second fraction comprising cyclohexylbenzene and phenol; (C) removing at least a portion of the phenol from at least a portion of the second fraction to obtain a third fraction; (D) recycling at least a portion of the cyclohexylbenzene in the third fraction to the oxidizing step (A); and (E) contacting at least a portion of the cyclohexyl-1-phenyl-1-hydroperoxide in the first fraction with an acid catalyst in a cleavage reactor under cleavage conditions to obtain a cleavage product comprising phenol and cyclohexanone.

23 Claims, 3 Drawing Sheets

PROCESS FOR MAKING PHENOL AND/OR CYCLOHEXANONE

PRIORITY CLAIM

This application is a National Stage Application of International Application No. PCT/US2014/061088 filed Oct. 17, 2014, which claims priority to U.S. Ser. No. 61/907,844, filed Nov. 22, 2013, the disclosures of which are incorporated herein by reference in their entirety. This application also claims priority to EP 14153808.2, filed Feb. 4, 2014.

FIELD

The present disclosure relates to a process for making phenol and/or cyclohexanone.

BACKGROUND

Phenol and cyclohexanone are important compounds in the chemical industry and are useful in, for example, the production of phenolic resins, bisphenol A, ε-caprolactam, adipic acid, and plasticizers.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. However, the world demand for phenol is growing more rapidly than that for acetone.

Thus, a process that uses higher alkenes instead of propylene as feed and coproduces higher ketones, such as cyclohexanone, rather than acetone may be an attractive alternative route to the production of phenols. There is also a growing demand for cyclohexanone.

It is known from, e.g., U.S. Pat. No. 6,037,513, that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof. This reference also discloses that the resultant cyclohexylbenzene can be oxidized to the corresponding hydroperoxide which can then be decomposed to produce phenol and cyclohexanone.

The oxidation of cyclohexylbenzene to produce cyclohexylbenzene hydroperoxide and the cleavage of cyclohexylbenzene hydroperoxide to produce phenol and cyclohexanone are much more complex than the cumene oxidation and cumene hydroperoxide cleavage in the Hock process. For example, the oxidation of cyclohexylbenzene is conducted at low conversion per pass to reduce the formation of undesirable by-products and optimize process yields. The residual cyclohexylbenzene is then typically separated from the cyclohexylbenzene hydroperoxide product and recycled to the oxidation reaction.

SUMMARY

It has been found that phenol is a significant by-product of the cyclohexylbenzene oxidation reaction. It has also been found that the presence of phenol at a high concentration is detrimental to the oxidation reaction since phenol acts as a free radical inhibitor quenching the oxidation reaction. It has also been found that phenol contained in recycle cyclohexylbenzene stream(s) can be excessively high and, if left unabated, can inhibit the oxidation reaction to an undesired degree. The present disclosure provides a process for reducing the phenol concentration in the recycle streams of cyclohexylbenzene oxidation.

Accordingly, in one aspect, the present disclosure relates to a process for making phenol and/or cyclohexanone, the process comprising:
(A) oxidizing a cyclohexylbenzene feed to obtain an oxidation product comprising cyclohexylbenzene, cyclohexyl-1-phenyl-1-hydroperoxide and phenol;
(B) separating at least a portion of the oxidation product to obtain a first fraction comprising cyclohexyl-1-phenyl-1-hydroperoxide and a second fraction comprising cyclohexylbenzene and phenol;
(C) removing at least a portion of the phenol from at least a portion of the second fraction to obtain a third fraction;
(D) recycling at least a portion of the cyclohexylbenzene in the third fraction to the oxidizing step (A); and
(E) contacting at least a portion of the cyclohexyl-1-phenyl-1-hydroperoxide in the first fraction with an acid catalyst in a cleavage reactor under cleavage conditions to obtain a cleavage product comprising phenol and cyclohexanone.

Step (B) may comprise subjecting at least a portion of the oxidation product to vacuum evaporation, for example at a temperature of no greater than 130° C. and an absolute pressure in a range from 0.05 to 3 kPa.

Step (C) may comprise contacting at least a portion of the second fraction with an aqueous composition comprising a base to produce an aqueous phase containing at least part of the phenol or a derivative thereof from the second fraction and an organic phase containing cyclohexylbenzene and having a reduced concentration of phenol as compared with the second fraction, and recovering at least a portion of the organic phase as the third fraction.

DETAILED DESCRIPTION

In the present disclosure, a process is described as comprising at least one "step." It should be understood that each step is an action or operation that may be conducted once or multiple times in the process, in a continuous or discontinuous fashion. Unless specified to the contrary or the context clearly indicates otherwise, each step in a process may be conducted sequentially in the order as they are listed, with or without overlapping with one or more other step(s), or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, steps are performed in the order listed.

Unless otherwise indicated, all numbers indicating quantities in the present disclosure are to be understood as being modified by the term "about" in all instances. It should also be understood that the precise numerical values used in the specification and claims constitute specific examples. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, processes using "a hydrogenation metal" include those where one, two or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific examples unless specified or indicated to the contrary.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in singular form, means mono substituted cyclohexylbenzene.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Non-limiting examples of materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

Supply of Cyclohexylbenzene

The cyclohexylbenzene supplied to oxidation step (A) of the process of the present disclosure can be supplied by chemical reactions of certain raw materials, such as those described below (e.g., a hydroalkylation reaction), and/or by recycling of residual cyclohexylbenzene not consumed in subsequent process steps where a cyclohexylbenzene-containing feed is subjected to a chemical reaction, such as oxidation.

The cyclohexylbenzene supplied to oxidation step (A) can be produced and/or recycled as part of an integrated process for producing phenol and cyclohexanone from benzene. In such an integrated process, benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

(Reaction-1)

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include palladium, ruthenium, nickel, zinc, tin, and cobalt, with palladium being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, $SnO$, $SnO_2$, and mixtures, combinations and complexes thereof.

Although the hydroalkylation reaction is highly selective towards cyclohexylbenzene, the effluent from the hydroalkylation reaction may contain some dialkylated products, unreacted benzene and cyclohexane. The unreacted benzene may be recovered by distillation and recycled to the reactor. The remaining effluent from benzene distillation may be further distilled to separate the monocyclohexylbenzene product from dicyclohexylbenzene and other heavies. Depending on the quantity of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 $hr^{-1}$ to 10 $hr^{-1}$ on total feed, and a benzene/dicyclohexylbenzene weight ratio of 1:1 to 5:1.

Dealkylation is also desirably effected in a reactor separate from the hydroalkylation reactor, such as a reactive distillation unit, at a temperature of about 150° C. to about 500° C. and a pressure of 15 to 500 psig (200 to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Oxidation of Cyclohexylbenzene

After removal of the unreacted benzene and the polyalkylated benzenes and other heavy species, the cyclohexylbenzene is fed to the oxidizing step (A), which can be conducted in one or more oxidation reactor(s). In the oxidation reactor(s), at least a portion of the cyclohexylbenzene contained in the oxidation feed is converted to cyclohexyl-1-phenyl-1-hydroperoxide, the desired hydroperoxide, according to the following Reaction-2:

(Reaction-2)

The feed supplied to the oxidizing step (A) may comprise cyclohexylbenzene at a concentration in a range from CON1 wt % to CON2 wt %, based on the total weight of the feed introduced into the oxidation reactor, where CON1 and CON2 can be, independently, 10, 20, 30, 40, 50, 60, 70, 80, 90, 92, 94, 95, 96, 97, 98, 99, 99.5, or even 99.9, or even higher, as long as CON1<CON2.

In addition, the feed to the oxidizing step (A) may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) phenylmethylcyclopentane, including one or more of 1-phenyl-1-methylcyclopentane, 1-phenyl-2-methylcyclopentane, and 1-phenyl-3-methylcyclopentane, at a total concentration in a range from 1 ppm to 2 wt %, such as from 10 ppm to 1 wt %; (iv) water at a concentration up to 5000 ppm, such as from 100 ppm to 1000 ppm; and (v) olefins or alkene benzenes, such as phenylcyclohexene, at a concentration no greater than 1000 ppm.

The feed to the oxidizing step (A) may also contain phenol since phenol has been found to be a significant by-product of the cyclohexylbenzene oxidation reaction. Hence, if not abated, phenol will be present in the residual cyclohexylbenzene recycled from the oxidizing step (A) and possibly the cleavage reaction (E). However, as discussed above, it is believed that the presence of phenol in the oxidation feed can inhibit the oxidation reaction and hence, as will be described in more detail below, the present process seeks to reduce the level of phenol in the oxidation feed to no greater than 50 ppm, desirably no greater than 10 ppm, based on the total weight of the feed. Preferably, the oxidation feed contains no detectable phenol.

In exemplary processes, the oxidizing step (A) may be accomplished by contacting an oxygen-containing gas, such as air and various derivatives of air, with the feed comprising cyclohexylbenzene. For example, a stream of $O_2$, pure air, or other $O_2$-containing mixtures can be pumped through the cyclohexylbenzene-containing feed in an oxidation reactor such as a bubble column to effect the oxidation.

The oxidation may be conducted in the absence or presence of a catalyst. Examples of suitable oxidation catalysts include those having a structure of formula (FC-I), (FC-II), or (FC-III) below:

where:
A represents a ring optionally comprising a nitrogen, sulfur, or oxygen in the ring structure, and optionally substituted by an alkyl, an alkenyl, a halogen, or a N-, S-, or O-containing group or other group;
X represents a hydrogen, an oxygen free radical, a hydroxyl group, or a halogen;
$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and
m is 0, 1 or 2.

Examples of particularly suitable catalysts for the oxidation step (A) include those represented by the following formula (FC-IV):

where:
$R^2$, the same or different at each occurrence, independently represents a halogen, a N-, S-, or O-containing group, or an optionally substituted linear or branched acyclic alkyl or cyclic alkyl group having 1 to 20 carbon atoms; and
n is 0, 1, 2, 3, or 4.

One especially suitable catalyst having the above formula (FC-IV) for the oxidation step (A) is NHPI (N-hydroxy phthalic imide). For example, the feed to oxidizing step (A) can comprise from 10 to 2500 ppm of NHPI by weight of the cyclohexylbenzene in the feed.

Non-limiting examples of suitable reaction conditions of the oxidizing step (A) include a temperature from 70° C. to 200° C., such as 90° C. to 130° C., and a pressure of 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step (A) may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series, each operating at the same or different conditions selected to enhance the oxidation reaction of reaction media with different compositions. The oxidation reactor may be operated in a batch, semi-batch, or continuous flow manner well known to those skilled in the art.

Composition of the Oxidation Product

Desirably, the oxidation product exiting the oxidation reactor contains cyclohexyl-1-phenyl-1-hydroperoxide at a concentration in a range from Chp1 wt % to Chp2 wt %, based on the total weight of the oxidation product, where Chp1 and Chp2 can be, independently, 5, 10, 15, 20, 25, 30, 35, 40, 45, 50, 55, 60, 65, 70, 75, 80, as long as Chp1<Chp2. Preferably, the concentration of cyclohexyl-1-phenyl-1-hydroperoxide in the oxidation product is at least 20% by weight of the oxidation product. The oxidation product may further comprise residual cyclohexylbenzene at a concentration in a range from Cchb1 wt % to Cchb2 wt %, based on the total weight of the oxidation product, where Cchb1 and Cchb2 can be, independently, 20, 25, 30, 35, 40, 45, 50, 55, 60, 65, 70, 75, 80, 85, 90, 95, as long as Cchb1<Cchb2. Preferably, the concentration of cyclohexylbenzene in the oxidation product is at most 65% by weight of the oxidation product.

In addition, the oxidation product may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in feed supplied to step (A), such as cyclohexyl-2-phenyl-1-hydroperoxide, and cyclohexyl-3-phenyl-1-hydroperoxide. These undesired hydroperoxides are present at a total concentration of at most 5 wt %, such as at most 3 wt %, 2 wt %, 1 wt %, or even 0.1 wt %. They are undesirable because they may not convert into phenol and cyclohexanone in the cleavage reaction at the desired conversion and/or selectivity, resulting in overall yield loss.

As noted above, the oxidation product also contains phenol as a further by-product of the oxidation reaction. The concentration of phenol (CPh) in the oxidation product exiting the oxidation reactor(s) can range from CPh1 ppm to CPh2 ppm, where CPh1 and CPh2 can be, independently:

50, 60, 70, 80, 90, 100, 150, 200, 250, 300, 350, 400, 450, 500, 550, 600, 650, 700, 750, 800, 850, 900, 950, 1000, 1500, 2000, as long as CPh1<CPh2.

The oxidation product invariably contains water because: (i) depending on the production method and source, the cyclohexylbenzene fed to step (A) can contain water at a certain level; and (ii) during the oxidation reaction, water is produced due to, inter alia, premature decomposition of the hydroperoxides produced. While a portion of the water contained in the reaction media in step (A) can be carried away if a stream of gas passes through the oxidation reaction medium and exits the oxidation reactor, some water will remain in the oxidation product. The concentration of water in the oxidation product exiting the oxidation reactor is C1a ppm by weight, based on the total weight of the oxidation product, which can range from C1a ppm to C1b ppm, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

The oxidation product may also contain part or all of any catalyst, such as NHPI, supplied to the oxidizing step (A). For example, the oxidation product may contain from 10 to 2500 ppm of NHPI, such as from 100 to 1500 ppm by weight of NHPI.

Treatment of the Oxidation Product

In the process of the present disclosure, before being supplied to the cleavage step (E), at least a portion of the oxidation product is separated into at least a first fraction comprising cyclohexyl-1-phenyl-1-hydroperoxide and a second fraction comprising cyclohexylbenzene and phenol. The first fraction typically has a higher concentration of cyclohexyl-1-phenyl-1-hydroperoxide than the second fraction. The second fraction typically has a higher concentration of cyclohexylbenzene than the first fraction.

The separation process may include subjecting at least a portion of the oxidation product to vacuum evaporation so as to recover a vapor phase comprising a major portion of the cyclohexylbenzene, phenol and other lower boiling components of the oxidation product portion. For example, water, if present in the oxidation product portion, will preferentially partition with the cyclohexylbenzene and phenol in the vapor phase. The majority of the cyclohexyl-1-phenyl-1-hydroperoxide and other higher boiling components of the oxidation product portion, such as other hydroperoxides and NHPI catalyst, if present in the oxidation product portion, will preferentially remain in the liquid phase first fraction. The vapor phase is then condensed to produce the desired second fraction in liquid phase.

Where vacuum evaporation is used to effect separation of the oxidation product, the first fraction may have a composition comprising:
cyclohexyl-1-phenyl-1-hydroperoxide at a concentration in a range from Chp3 wt % to Chp4 wt %, based on the total weight of the first fraction, where Chp3 and Chp4 can be, independently, 45, 50, 55, 60, 65, 70, 75, 80, 85, 90, as long as Chp3<Chp4;
cyclohexylbenzene at a concentration in a range from Cchb3 wt % to Cchb4 wt %, based on the total weight of the first fraction, where Cchb3 and Cchb4 can be, independently, 10, 15, 20, 25, 30, 35, 40, 45, 50, 55, as long as Cchb3<Cchb4;
phenol at a concentration of CPh3 ppm to CPh4 ppm, where CPh3 and CPh4 can be, independently: 0, 5, 10, 15, 20, 25, 30, 40, 50, 100, as long as CPh3<CPh4; and
water at a concentration of C2a ppm to C2b ppm, where C2a and C2b can be, independently: 0, 5, 10, 15, 20, 25, 30, 35, 40, 45, as long as C2a<C2b;
and the second fraction may have a composition comprising:
cyclohexylbenzene at a concentration in a range from Cchb5 wt % to Cchb6 wt %, based on the total weight of the second fraction, where Cchb5 and Cchb6 can be, independently, 85, 86, 87, 88, 89, 90, 93, 95, 99, as long as Cchb5<Cchb6;
phenol at a concentration of CPh5 ppm to CPh6 ppm, based on the total weight of the second fraction, where CPh5 and CPh6 can be, independently: 100, 150, 200, 250, 300, 350, 400, 450, 500, 550, 600, 650, 700, 750, 800, 850, 900, 950, 1000, 1500, 2000, as long as CPh5<CPh6; and
cyclohexyl-1-phenyl-1-hydroperoxide at a concentration in a range from Chp5 wt % to Chp6 wt %, based on the total weight of the second fraction, where Chp5 and Chp6 can be, independently: 0, 0.1, 0.5, 1, 1.5, 2, 2.5, 5, 7.5, 10, as long as Chp5<Chp6.

Desirably, the concentration of cyclohexyl-1-phenyl-1-hydroperoxide in the first fraction can be at least 50 wt %, while the concentration of cyclohexylbenzene in the first fraction is at most 50 wt %, both concentrations being based on the total weight of the first fraction.

Advantageously, the concentration of cyclohexyl-1-phenyl-1-hydroperoxide in the second fraction can be at most 5 wt %, while the concentration of cyclohexylbenzene in the second fraction can be at least 95 wt %, both concentrations being based on the total weight of the second fraction.

Because cyclohexylbenzene hydroperoxide is prone to decomposition at elevated temperatures, e.g., at above 150° C., the vacuum evaporation step to separate the oxidation product into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation product, the oxidation product is subjected to a very low absolute pressure, e.g., in a range from Pc1 kPa to Pc2 kPa, where Pc1 and Pc2 can be, independently, 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation product portion into first and second fractions, part or all of the first fraction can be routed directly to the cleavage step (E). Thus, although water can be detrimental to the cleavage step, the concentration of water in the first fraction remaining after the vacuum evaporation is typically sufficiently low to obviate the need for further water reduction. All or a portion of the first fraction may be cooled before passage to the cleavage step (E) so as to cause crystallization of the unreacted imide oxidation catalyst. The imide crystals may then be recovered for reuse either by filtration or by scraping from a heat exchanger surface used to effect the crystallization.

In accordance with the present process, the second fraction produced from the oxidation effluent is treated to reduce the level of phenol therein before part or all of the cyclohexylbenzene in the second fraction is recycled to the oxidizing step (A).

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, of one or more of a corresponding carbonate, bicarbonate, or carbonate-hydroxide complex.

Desirably, the aqueous composition comprising the base has a pH of at least 8, preferably at least 10. Generally, the contacting of the aqueous base composition with the second fraction is conducted such that the molar ratio of the total amount of the base in the aqueous composition supplied to contact the second fraction to the total amount of phenol in the second fraction is in a range from Rm1 to Rm2, where Rm1 and Rm2 can be, independently: 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, as long as Rm1<Rm2. Such a molar ratio assists in maintaining the reaction between phenol and the base such that the phenol is driven from the organic phase to the aqueous phase because of the higher solubility in water of the phenoate salt than phenol per se, resulting in substantially complete removal of phenol from the second fraction.

The aqueous base composition can take the form of a solution, an emulsion, or a suspension, a colloid, or other dispersion forms. Preferably, the aqueous base composition is an aqueous solution.

The contacting between the second fraction and the aqueous base composition is desirably conducted in a liquid-liquid extraction device at a temperature from Te1° C. to Te2° C., where T1 and T2 can be, independently, 10, 12, 14, 15, 16, 18, 20, 22, 25, 28, 30, 35, 40, 45, 50, 55, 60, 62, 64, 65, 66, 68, 70, 72, 74, 75, 78, 80, as long Te1<Te2. Desirably, the concentration of cyclohexylbenzene in the first fraction is in a range from Cchb1 wt % to Cchb2 wt %, where Cchb1 and Cchb2 can be, independently, 30, 35, 40, 45, 50, 55, 60, 65, 70, 75, 80, 85, 90, 95, 97, 98, 99, as long as Cchb1<Cchb2. Examples of suitable liquid-liquid extraction devices comprise sieve tray columns, spray columns, packed columns, rotating disc contactors, mixer-settlers and combinations of these devises.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step (A) as a third fraction either directly, or more preferably, after water washing to remove base entrained in the organic phase. Water washing is also desirably conducted in a liquid-liquid extraction device, which may be in a separate stage of the same liquid-liquid extraction device used for the base treatment step or in a separate liquid-liquid extraction device. Again, suitable liquid-liquid extraction devices for the washing step include sieve tray columns, spray columns, packed columns, rotating disc contactors, mixer-settlers and combinations of these devices.

The water-washed third fraction is rich in cyclohexylbenzene and depleted in phenol and can be recycled to the oxidizing step (A) with or without drying. However, it is desirable to initially pass the water-saturated third fraction through either coalescence media (crinkle wire mesh) or a separate coalescer vessel to break up any possible emulsions or small (<100 micron) droplets before the third fraction enters the oxidation reactor, especially if the third fraction is to be recycled to the oxidizing step (A) without drying. Coalescence can be conducted in a separate drum. Some of the inventory of the drum may be recycled to the upstream liquid-liquid extraction device(s), for example a sieve tray column, to improve column stability and operability by controlling flowrate.

Cleavage Reaction

As discussed above, the present process also includes the step of cleaving at least a portion of the cyclohexylbenzene hydroperoxide contained in the first fraction of the oxidation product in the presence of an acid catalyst to produce a cleavage product mixture comprising the acid catalyst, phenol, and cyclohexanone. As used herein, "cleaving" means causing a cleavage reaction to occur. In the cleavage reaction, at least a portion of the cyclohexyl-1-phenyl-1-hydroperoxide decomposes in high selectivity to cyclohexanone and phenol, and further, other hydroperoxides present may decompose to form various products, discussed below.

The acid catalyst can be at least partially soluble in the cleavage reaction mixture, is stable at a temperature of at least 185° C. and has a lower volatility (higher normal boiling point) than cyclohexylbenzene. The acid catalyst can be also at least partially soluble in the cleavage product mixture.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

As a result of potentially high amounts of cyclohexylbenzene in the cleavage reaction mixture, considerably higher than cumene in the Hock process material undergoing a cleavage reaction, it may be convenient in the present process to use more acid catalyst to effect the cleavage reaction than typically believed optimal in the Hock process, to at least partially overcome the insolubility of the acid in the cleavage reaction mixture. However, lower amounts of acid catalyst may also be used in the present process, with appropriate additional cleavage reactor volume and residence time of the cleavage reaction mixture in the cleavage reactor to obtain high hydroperoxide conversion.

The cleavage reaction occurs under cleavage conditions including a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

The cleavage reaction mixture can contain the acid catalyst at a concentration in a range from Cac1 ppm to Cac2 ppm by weight of the total weight of the cleavage reaction mixture, where Cac1 and Cac2 can be, independently, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Preferably, Cac1 is 50, and Cac2 is 200.

Conversion of hydroperoxides, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given hydroperoxide, or of all hydroperoxides present in the portion of the first fraction undergoing the cleavage reaction. This is desirable because any hydroperoxide, even the cyclohexyl-1-phenyl-1-hydroperoxide, becomes a contaminant in the cleavage product mixture and treated cleavage product mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone according to the following desired Reaction-3:

(Reaction-3)

Desirably, each mole of cyclohexyl-1-phenyl-1-hydroperoxide produces one mole of phenol and one mole of cyclohexanone. However, due to side reactions, the selectivity of the cleavage reaction to phenol can range from Sph1% to Sph2% and the selectivity to cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation product, the cleavage reaction mixture may further comprise other added materials, such as the cleavage catalyst, a solvent, and one or more products of the cleavage reaction such as phenol and cyclohexanone recycled from the cleavage product mixture, or from a downstream separation step. Thus, the cleavage reaction mixture inside the cleavage reactor may comprise, based on the total weight of the cleavage reaction mixture: (i) phenol at a concentration from CPh9 wt % to CPh10 wt %, where CPh9 and CPh10 can be, independently, 20, 25, 30, 35, 40, 45, 50, 55, 60, 65, 70, 75, or 80, as long as CPh9<CPh10; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; and (iii) cyclohexylbenzene at a concentration from Cchb7 wt % to Cchb8 wt %, where Cchb7 and Cchb8 can be, independently, 5, 8, 9, 10, 12, 14, 15, 18, 20, 22, 24, 25, 26, 28, 30, 35, 40, 45, 50, 55, 60, 65, 70, as long as Cchb7<Cchb8.

As used herein, a "contaminant" or a "contaminant byproduct" may include any unwanted hydrocarbon or oxygenated hydrocarbon component in the cleavage product mixture or the neutralized cleavage product mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage product mixture or the neutralized cleavage product mixture, or any portion thereof may have been produced in any step of the present process, or may have been contained in the feed comprising cyclohexylbenzene undergoing oxidation. For example, a contaminant may be present in the cleavage product mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation product from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. The cleavage reactor may comprise a plurality of reactors in series, each performing a portion of the conversion reaction, optionally operating in different modes and at different conditions selected to enhance the cleavage reaction at the pertinent conversion range. The cleavage reactor can be a catalytic distillation unit.

The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting cleavage reactor may comprise, based on the total weight of the cleavage product mixture: (i) phenol at a concentration from CPh11 wt % to CPh12 wt %, where CPh11 and CPh12 can be, independently, 20, 25, 30, 35, 40, 45, 50, 55, 60, 65, 70, 75, or 80, as long as Ch11<CPh12; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; and (iii) cyclohexylbenzene at a concentration from Cchb9 wt % to Cchb10 wt %, where Cchb9 and Cchb10 can be, independently, 5, 8, 9, 10, 12, 14, 15, 18, 20, 22, 24, 25, 26, 28, 30, 35, 40, 45, 50, 55, 60, 65, 70, as long as Cchb9<Cchb10.

At least a portion of the cleavage product mixture may be subjected to a neutralization reaction, which may include all or some fraction of the cleavage product mixture as directly produced without undergoing any separation (e.g., some fraction resulting from diverting some amount of the cleavage reaction mixture as directly produced to another disposition, such as temporary storage). Thus, the at least a portion of the cleavage product mixture may have the same composition as the cleavage product mixture. Further, all or some of the cleavage product mixture as directly produced may undergo one or more separations, and an appropriate product of that separation (or separations), now modified in composition relative the cleavage product mixture as directly produced, may provide the at least a portion of the cleavage product mixture subjected to the neutralization reaction.

The cyclohexylbenzene contained in the cleavage product mixture can be separated from other major components, such as phenol and cyclohexanone by, e.g., distillation. The separated cyclohexylbenzene can then be treated and/or purified before being delivered to oxidizing step (A) along with cyclohexylbenzene supplied from other resources, such as fresh cyclohexylbenzene produced in the hydroalkylation reactor and recycled cyclohexylbenzene from the third fraction discussed above. Since the cyclohexylbenzene separated from the cleavage product mixture may contain phenol, the material may be subjected to treatment with an aqueous composition comprising a base as described above for the second fraction of the oxidation. Reduction of the level of phenol in the cyclohexylbenzene separated from the cleavage product mixture can be additionally or alternatively effected by a process comprising hydrogenation as disclosed in, for example, WO2011/100013, the entire contents of which are incorporated herein by reference.

Contaminant Treatment

As discussed above, the cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

The present invention will now be more particularly described with reference to the drawings which provide non-limiting examples of different liquid-liquid extraction processes using different types of devices. As used herein, the term "caustic" means one or more of LiOH, NaOH, KOH, RbOH, $Mg(OH)_2$, $Ca(OH)_2$, $Sr(OH)_2$, $Ba(OH)_2$.

Figure 1:
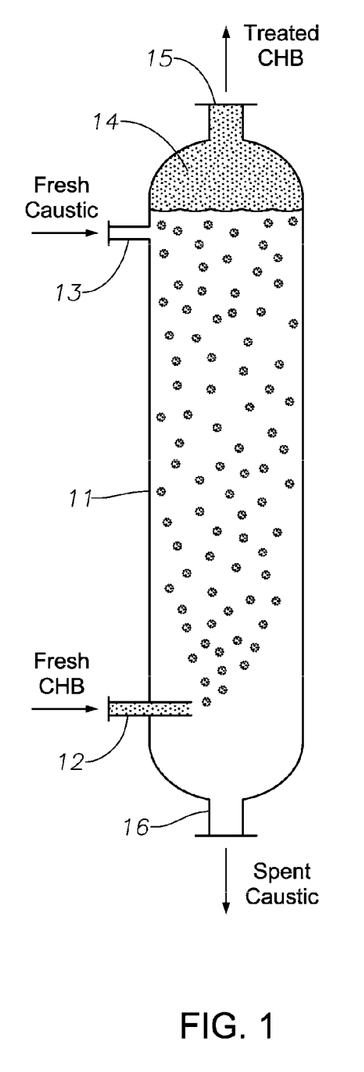
FIG. 1 is a schematic drawing of part of an exemplary process for making phenol and/or cyclohexanone of the present disclosure in which a spray column is used for the phenol removing step (C).

Referring to FIG. 1, in a first example, the liquid-liquid extraction device comprises a spray column contactor 11 without any internals or packing. The second fraction of the oxidation product is injected as a liquid through a distributor nozzle 12 located adjacent the bottom of the column 11, while a caustic dispersion is injected through an inlet 13 located adjacent the top of the column 11. Due to lower density, cyclohexylbenzene rises naturally through the continuous aqueous phase to form a layer 14 of coalesced, phenol-depleted cyclohexylbenzene, which can be removed through a first outlet 15 provided at the top of the column 11. The caustic dispersion flows counter-current to the cyclohexylbenzene phase, but will generally be highly backmixed because of the lack of internals. The spent caustic dispersion is removed through a second outlet 16 at the bottom of the column 11.

A second stage water wash of the phenol-depleted cyclohexylbenzene phase can be effected in a separate spray column (not shown), or stacked on top of the first stage caustic wash with a nozzle allowing the phenol-depleted cyclohexylbenzene to cross flow between the two stages.

Figure 2:
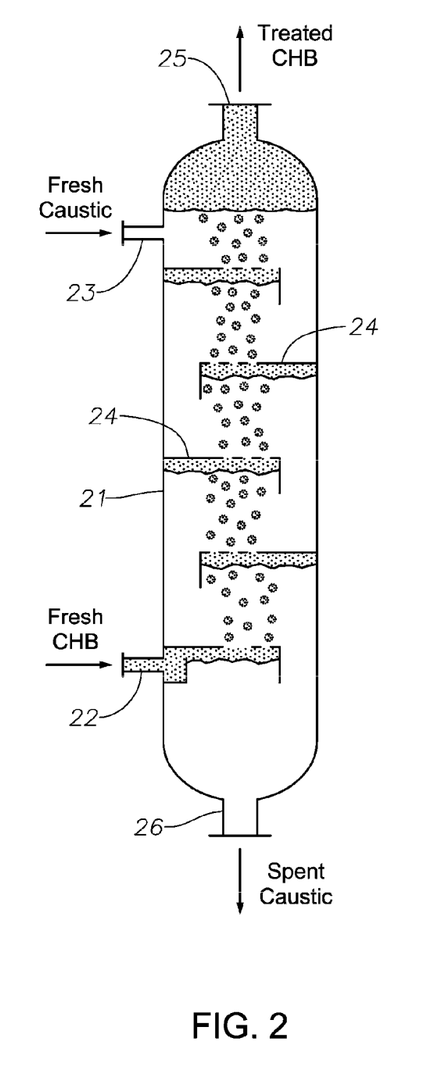
FIG. 2 is a schematic drawing of part of a second exemplary process for making phenol and/or cyclohexanone of the present disclosure in which a sieve tray column is used for the phenol removing step (C).

Referring to FIG. 2, in a second example, the liquid-liquid extraction device comprises a sieve tray column 21. As in the FIG. 1 example, the second fraction of the oxidation product is injected as a liquid through a first inlet 22 located adjacent the bottom of the column 21, while a caustic dispersion is injected through a second inlet 23 located adjacent the top of the column 21. The sieve tray column 21 is conceptually similar to the spray column 11, but incorporates a series of sieve trays 24 to stage the column to ensure true counter-current contacting between the organic and aqueous phases. Holes in the trays 24 allow cyclohexylbenzene droplets to rise and contact cross-flowing aqueous caustic phase until they coalesce to form an organic layer underneath the next sieve tray. Interfacial area is created by the hydrostatic head of the cyclohexylbenzene layer underneath the trays, providing the pressure drop needed to generate droplets through the holes. This offers significant operating flexibility and stability to varying process rates. Phenol-depleted cyclohexylbenzene organic phase is removed through a first outlet 25 provided at the top of the column 21, while spent caustic is removed through a second outlet 26 at the bottom of the column 21.

As with the spray column, a second stage water wash can be effected in a separate sieve tray column or a stacked column with a nozzle separating the two stages.

Figure 3:
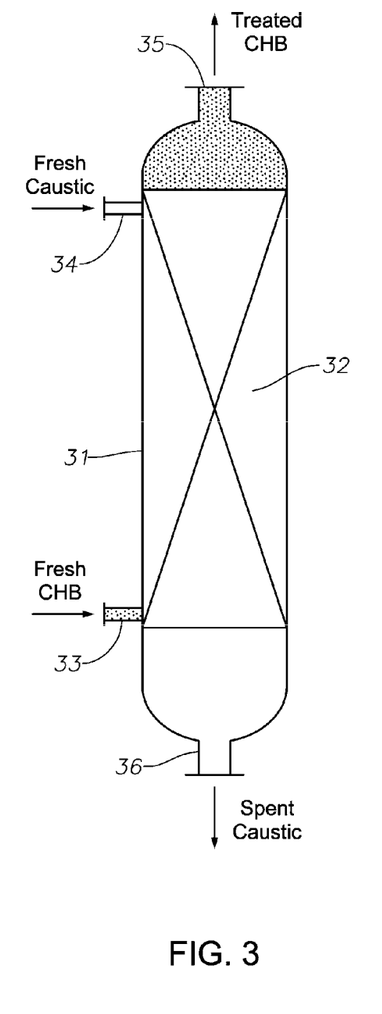
FIG. 3 is a schematic drawing of part of a third exemplary process for making phenol and/or cyclohexanone of the present disclosure in which a packed column is used for the phenol removing step (C).

FIG. 3 illustrates a third example, in which the liquid-liquid extraction device comprises a packed column 31. Structured or random packing 32 is included in column 31 to provide structure for the liquid-liquid interface. In this case, the two liquid phases are bicontinuous, creating a different type of interfacial area and film thickness for mass transfer than the spray and sieve tray columns 11 and 21. As before, the second fraction of the oxidation product is injected through a first inlet 33 located adjacent the bottom of the column 31, while a caustic dispersion is injected through a second inlet 34 located adjacent the top of the column 31. Similarly, phenol-depleted cyclohexylbenzene organic phase is removed through a first outlet 35 provided at the top of the column 31, while spent caustic is removed through a second outlet 36 at the bottom of the column 31.

Again, water wash may be conducted in a separate packed column or in the same vessel with an added stage.

Figure 4:
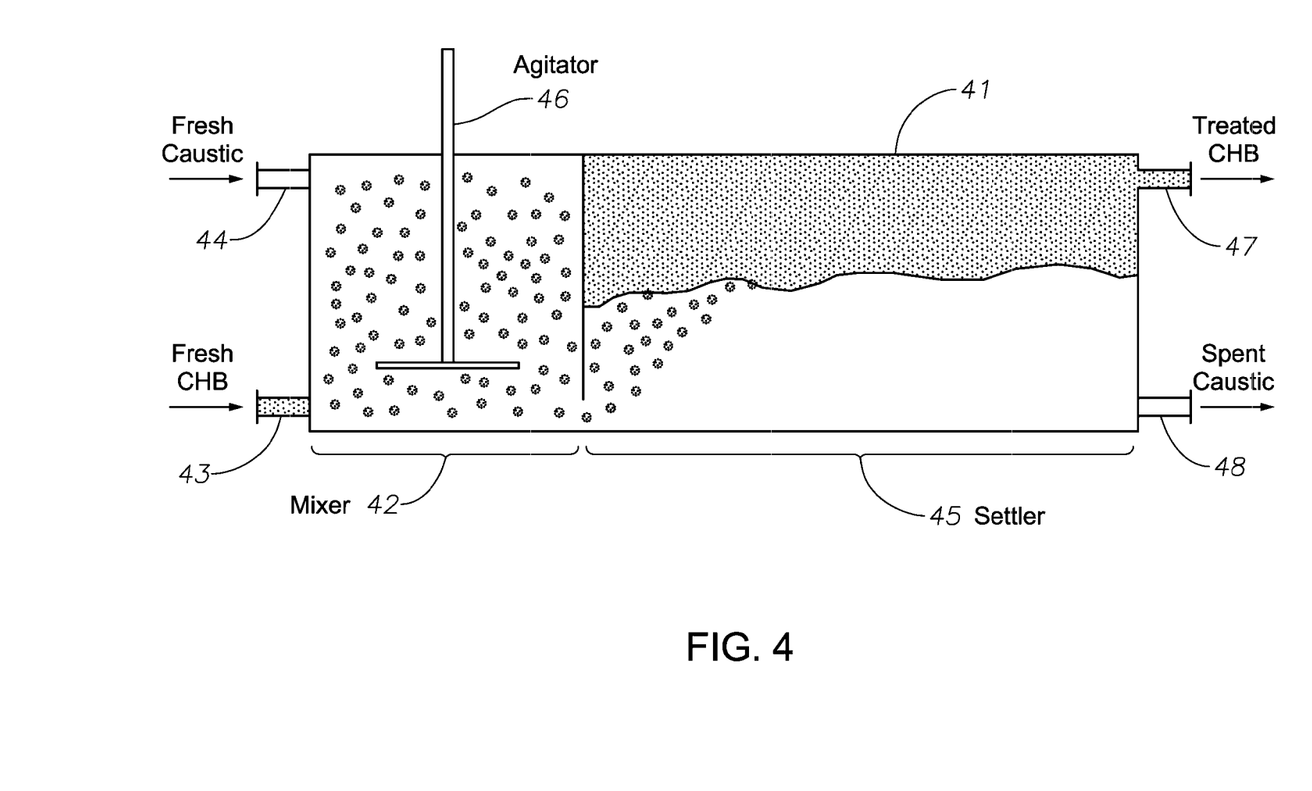
FIG. 4 is a schematic drawing of part of a fourth exemplary process for making phenol and/or cyclohexanone of the present disclosure in which a mixer-settler is used for the phenol removing step (C).

FIG. 4 illustrates a fourth example, in which the liquid-liquid extraction device comprises a mixer-settler 41. In this example, the liquid-liquid contacting is conducted in a mechanically-agitated system such as a mixer tank 42, which receives the second fraction of the oxidation product through a first inlet 43 located adjacent the bottom of the tank 41 and a caustic solution through a second inlet 44 located adjacent the top of the tank 41. After agitation in the mixing tank, the resulting organic/caustic mixture flows to a settler section 45 which allows the two liquid phases to phase-separate. The settler section 45 may be in a separate vessel than the mixer, or in the same vessel, located horizontally adjacent (shown in FIG. 4) or vertically above the mixer tank 42. The interfacial area for mass transfer in the mixer tank 42 is generated by the power input from a mechanical agitator 46. The coalescence zone in the settler section 43 must be sized to allow sufficient distance to achieve the separation between the organic phase, which is removed through a first outlet 47 located adjacent the top of the settler section 43, and the aqueous phase, which is removed through a second outlet 48 located adjacent the bottom of the settler section 43.

Figure 5:
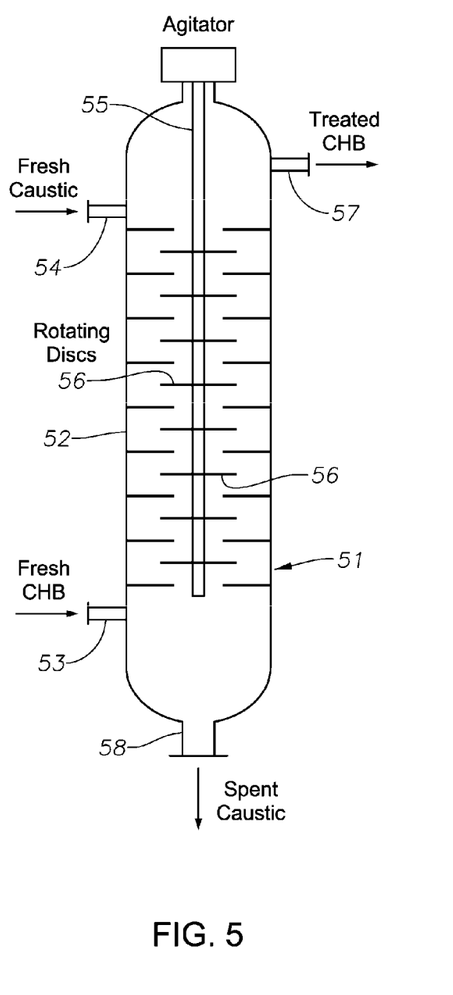
FIG. 5 is a schematic drawing of part of a fifth exemplary process for making phenol and/or cyclohexanone of the present disclosure in which a rotating disc contactor is used for the phenol removing step (C).

FIG. 5 illustrates a fifth example, in which the liquid-liquid extraction device comprises a rotating disc contactor 51. The contactor 51 is housed within a column 52, which receives the second fraction of the oxidation product through a first inlet 53 located adjacent the bottom of the column 51 and a caustic dispersion through a second inlet 54 located adjacent the top of the column 51. Counter-current flow between the liquids is maintained, but the interfacial area for mass transfer is generated through the rotation of a shaft 55 with attached discs 56 to shear the liquids. Thus, the interfacial area generated is directly connected to the mixing power provided, just as with a mixer-settler of FIG. 4. Phenol-depleted cyclohexylbenzene phase is removed through a first outlet 57 provided adjacent the top of the column 51, while spent caustic is removed through a second outlet 58 at the bottom of the column 51.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for making phenol and/or cyclohexanone, the process comprising:
(A) oxidizing a cyclohexylbenzene feed to obtain an oxidation product comprising cyclohexylbenzene, cyclohexyl-1-phenyl-1-hydroperoxide and phenol;
(B) separating at least a portion of the oxidation product to obtain a first fraction comprising cyclohexyl-1-phenyl-1-hydroperoxide and a second fraction comprising cyclohexylbenzene and phenol;
(C) removing at least a portion of the phenol from at least a portion of the second fraction to obtain a third fraction;
(D) recycling at least a portion of the cyclohexylbenzene in the third fraction to the oxidizing step (A); and
(E) contacting at least a portion of the cyclohexyl-1-phenyl-1-hydroperoxide in the first fraction with an acid catalyst in a cleavage reactor under cleavage conditions to obtain a cleavage product comprising phenol and cyclohexanone.

2. The process of claim 1, wherein the separating step (B) comprises:
(B1) subjecting at least a portion of the oxidation product to vacuum evaporation to obtain a vapor phase; and
(B2) condensing the vapor phase to produce the second fraction.

3. The process of claim 2, wherein the vacuum evaporation is conducted at a temperature of no greater than 130° C. and an absolute pressure in a range from 0.05 to 3 kPa.

4. The process of claim 1, wherein the removing step (C) comprises:
(C1) contacting at least a portion of the second fraction with an aqueous composition comprising a base to produce an aqueous phase containing at least part of the phenol from the second fraction or a derivative thereof and an organic phase containing cyclohexylbenzene and having a reduced concentration of phenol as compared with the second fraction; and
(C2) recovering at least a portion of the organic phase as the third fraction.

5. The process of claim 4, wherein the base used in step (C1) has a $pK_b$ value less than 3.

6. The process of claim 4, wherein the pH of the aqueous composition used in step (C1) is at least 8.

7. The process of claim 4, wherein the molar concentration of the base in the aqueous composition is greater than the molar concentration of phenol in the second fraction.

8. The process of claim 4, wherein the base comprises a hydroxide of an alkali metal and/or a hydroxide of an alkaline earth metal.

9. The process of claim 4, wherein the contacting step (C1) comprises contacting the second fraction with the aqueous composition in a liquid-liquid extraction device.

10. The process of claim 9, wherein the liquid-liquid extraction device comprises at least one of a sieve tray column, a spray column, a packed column, a rotating disc contactor and a mixer-settler.

11. The process of claim 4, wherein the removing step (C) further comprises:
(C3) washing the organic phase with water before recovering the third fraction.

12. The process of claim 11, wherein the removing step (C) further comprises:
(C4) subjecting the third fraction to a coalescing step to assist phase separation of the third fraction.

13. The process of claim 1, wherein:
the oxidation product comprises phenol at a concentration of CPh1 ppm by weight;
the third fraction comprises phenol at a concentration of CPh2 ppm by weight; and
CPh1/CPh2≥2.0.

14. The process of claim 13, wherein CPh2 is less than 50.

15. The process of claim 1, wherein the concentration of cyclohexyl-1-phenyl-1-hydroperoxide in the oxidation product is at least 20 wt %, the concentration of cyclohexyl-1-phenyl-1-hydroperoxide in the first fraction is at least 50 wt % and the concentration of cyclohexyl-1-phenyl-1-hydroperoxide in the second fraction is at most 5 wt %.

16. The process of claim 1, wherein the concentration of cyclohexylbenzene in the oxidation product is at most 65 wt %, the concentration of cyclohexylbenzene in the first fraction is at most 50 wt %, and the concentration of cyclohexylbenzene in the second fraction is at least 95 wt %.

17. The process of claim 1, wherein the cleavage product comprises cyclohexylbenzene, and the process further comprises:
(F) separating a fourth fraction comprising cyclohexylbenzene and at least some phenol from the cleavage product;
(G) removing at least a portion of the phenol from the fourth fraction to obtain a fifth fraction; and
(H) recycling at least a portion of the cyclohexylbenzene in the fifth fraction to the oxidation step (A).

18. The process of claim 17, wherein the removing steps (C) and step (G) are combined into a single operation.

19. The process of claim 17, wherein the removing step (G) comprises:
(G1) contacting at least a portion of the fourth fraction with an aqueous composition comprising a base to produce an aqueous phase containing at least part of the phenol from the fourth fraction or a derivative thereof and an organic phase containing cyclohexylbenzene and having a reduced concentration of phenol as compared with the fourth fraction; and (G2) recovering at least a portion of the organic phase as the fifth fraction.

20. The process of claim 17, wherein the removing step (G) comprises hydrogenation of the fourth fraction.

21. The process of claim 1, wherein in step (A), an oxidation catalyst having a structure of formula (FC-I), (FC-II), or (FC-III) below is used:

where:

A represents an optionally substituted ring;

X represents a hydrogen, an oxygen free radical, a hydroxyl group, or a halogen;

$R^1$, the same or different at each occurrence, independently represents a halogen, a N-, S-, or O-containing group, or an optionally substituted linear or branched acyclic alkyl or cyclic alkyl group having 1 to 20 carbon atoms; and m is 0, 1 or 2.

22. The process of claim 1, wherein in step (A), an oxidation catalyst having a structure of formula (FC-IV) is used:

where:

$R^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

23. The process of claim 1, wherein in step (A), N-hydroxyl phthalmic imide is used as an oxidation catalyst.

* * * * *